United States Patent [19]

Kamakura et al.

[11] Patent Number: 4,981,798

[45] Date of Patent: Jan. 1, 1991

[54] IMMOBILIZATION OF GROWING MICROORGANISMS ON POLYMER-COATED COTTON GAUZE

[75] Inventors: Minoru Kamakura; Masao Tamada; Noboru Kasai; Isao Kaetsu, all of Gunma; Shigeru Yamanaka, Kanagawa, all of Japan

[73] Assignee: Japan Atomic Energy Research Institute, Tokyo, Japan

[21] Appl. No.: 388,760

[22] Filed: Aug. 1, 1989

Related U.S. Application Data

[63] Continuation-in-part of Ser. No. 148,118, Jan. 19, 1988, abandoned, which is a continuation-in-part of Ser. No. 928,588, Nov. 10, 1986, abandoned, which is a continuation of Ser. No. 707,218, Mar. 1, 1985, abandoned.

[30] Foreign Application Priority Data

Jun. 29, 1984 [JP] Japan .................... 59-134550

[51] Int. Cl.$^5$ ............... C12N 11/12; C12N 11/08; C12N 1/14; C12P 19/14
[52] U.S. Cl. .................... 435/179; 435/99; 435/177; 435/180; 435/945
[58] Field of Search ............ 435/174, 178, 179, 180, 435/181, 182, 99, 945

[56] References Cited

U.S. PATENT DOCUMENTS

| | | | |
|---|---|---|---|
| 3,809,605 | 5/1974 | Schmitt et al. | 435/179 |
| 3,824,150 | 7/1974 | Lilly et al. | 435/179 X |
| 3,860,490 | 1/1975 | Guttag | 435/182 |
| 3,933,589 | 1/1976 | Keyes | 435/181 |
| 4,000,098 | 12/1976 | Hofstee | 435/178 |
| 4,013,514 | 3/1977 | Wildi et al. | 435/179 X |
| 4,338,401 | 7/1982 | Cremonesi | 435/178 |
| 4,487,831 | 12/1984 | Day et al. | 435/99 |

FOREIGN PATENT DOCUMENTS

| | | | |
|---|---|---|---|
| 0122039 | 7/1983 | Japan | 435/180 |
| 0042889 | 3/1984 | Japan | 435/179 |
| 59-42889 | 3/1984 | Japan | 435/179 |

OTHER PUBLICATIONS

*Chamber's Technical Dictionary,* Third Edition, 1961, p. 27, The MacMillan Company.
*Encyclopedia of Chemical Technology,* Third Edition, vol. 19, 1982, pp. 608-609, Kirk-Othmer.
Hawley, *The Condensed Chemical Dictionary,* Van Nostrand Reinhold Company, 1977, pp. 741, 742.
Birnbaum et al., Immobilized Cells, Solid Phase Biochemistry, John Wiley & Sons, N.Y., 1983, pp. 629 & 695-704.

*Primary Examiner*—David M. Naff
*Attorney, Agent, or Firm*—Browdy and Neimark

[57] ABSTRACT

A carrier for immobilization of microorganisms is prepared by impregnating a fabric such as cotton gauze having a mesh size of 10-50 with 20-50% by weight of a vinyl monomer such as ethlene glycol methacrylate and polymerizing the monomer with ionizing radiation to form a polymer coating on the fabric. A microorganism such as *Trichoderma reesei* is grown in a liquid culture medium in contact with the polymer-coated fabric and the polymer-coated fabric is recovered containing growing cells of the microorganism. The polymer-coated fabric has high air permeability and permits good diffusion of liquid culture medium.

3 Claims, No Drawings

IMMOBILIZATION OF GROWING MICROORGANISMS ON POLYMER-COATED COTTON GAUZE

This application is a continuation-in-part of application Ser. No. 07/148,118, filed Jan. 19, 1988, now abandoned, which is a continuation-in-part of application Ser. No. 06/928,588, filed Nov. 10, 1988, now abandoned, which is a continuation of application Ser. No. 06/707,218, filed March 1, 1985, now abandoned.

BACKGROUND OF THE INVENTION

1. Field of the Invention

The present invention relates to an immobilized microorganism and a process for preparing the same. More particularly, the invention relates to a growing microorganism immobilized on a carrier made of a polymer-reinforced fabric having a network structure, and a process for preparing the same. The present invention is applicable to many fields such as the food industry, the pharmaceutical industry and medical care.

2. Description of the Prior Art

Fungi, bacteria, Actinomycetes and other microorganisms are extensively used in the food and pharmaceutical industries and in medical care, and the importance of these "bio" industries is constantly increasing. Conventionally, microorganisms used in these fields are treated in a batch system wherein the microorganisms are dispersed in a liquid culture medium. One major disadvantage with this batch system is its low utilization of the microorganism of interest because of the need to recover the end product from the microorganism in each batch culture. In order to solve this problem, considerable effort is being made forwards "immobilizing" a microorganism in a carrier such as a polymer gel by either binding or encapsulation techniques, so that the microorganism can be used in continuous cultivation. However, the conventional technique of using a polymer gel as a carrier is not applicable to aerobic microorganisms since their growth is appreciably limited by the inadequacy of air permeation into the carrier and insufficient diffusion of the liquid culture medium. Therefore, it has long been desired to develop a carrier which has high air permeability and permits good diffusion of a liquid culture medium and which is hence suitable for use in continuous cultivation of aerobic microorganisms.

SUMMARY OF THE INVENTION

It is an object of the present invention to provide a growing microorganism which is immobilized on a carrier made of a polymer-reinforced fabric having a network-like structure.

It is another object of the present invention to provide a process for preparing an immobilized growing microorganism, which comprises impregnating a fabric having a network-like structure with a polymerizable vinyl monomer, reinforcing said carrier with a polymer of said monomer prepared by its polymerization with an ionizing radiation, bringing said carrier into contact with a liquid culture medium in which a microorganism is capable of growing, inoculating said medium with the microorganism, and culturing the same.

It is further object of the present invention to provide a process for preparing a growing microorganism which is immobilized on a polymer-reinforced fabric having a network-like structure, said process comprising preparing a system having a fabric with a network-like structure, a polymerizable vinyl monomer and microorganism in a contact relationship, and polymerizing said monomer.

Other objects and advantages of the present invention may become apparent to those skilled in the art from the following description and disclosure.

Description of the Preferred Embodiment

The fabric with a network-like structure used as a carrier in the present invention is a knitted, woven or braided fabric made of a suitable fibrous material for knitting, weaving or braiding. The fibers from which the fabric with a network-like structure for use in the present invention is prepared may be single fibers which are natural, regenerated or synthetic, or they may be mixed to form blend yarns, or twisted together to form ply yarns or inter-woven or braided to form union fabrics. Such "composite" yarns may be used for the purpose of overcoming the disadvantage of a single fiber with the advantage of another fiber, thereby providing better yarns. The fabric used as a carrier in the present invention may be prepared by knitting, weaving or braiding the fibrous materials listed above, so long as the fabric has a networklike structure. The term "network-like structure" as used herein means that the fibers are not closely packed in the fabric and this term is not intended to restrict the usable fabric to plain fabrics. A typical example of the fabric with a network-like structure that can be used in the present invention is cotton gauze having 10–50 mesh, preferably 20–30 mesh.

The term "microorganism" as used herein covers a group of microorganisms producing filametous cells and it includes fungi, bacteria and Actinomycetes excluding "yeast type" fungi whose growth principally depend on asexual reproduction by germination and bacteria that grow by binary fission. Illustrative examples are fungi that belong to molds and Basidiomycetes, as well as bacteria such as mycobacteria and filamentous algae.

Since one of the essential elements of the present invention is to use as a microorganism immobilizing carrier a fabric with a network-like structure which is reinforced with a polymer, so in the following, the method for reinforcing such fabric with a polymer is explained. According to the present invention, the fabric with a network-like structure is first impregnated with hydrophobic polymerizable vinyl monomers, and thereafter, said monomer is polymerized by a suitable technique to form a polymer which adequately reinforces the fabric for use as a microorganism-immobilizing carrier. In this method, the fabric with a network-like structure is impregnated with 20–50% (w/w) of the vinyl monomer. This range has been determined as a result of the extensive studies the present inventors made with, respect to the correlation between the growth dynamics of microorganisms, organisms, the degree of polymer reinforcement of the fabric with a network structure, and the residual amount of mesh in the reinforced fabric. If the fabric is impregnated with less than 20% (w/w) of the monomer, the fibers in the fabric are not sufficiently reinforced to provide high mechanical strength, and the resulting carrier will easily deform during cultivation of the immobilized microorganism. If, on the other hand, the fabric is impregnated with more than 50% (w/w) of the monomer, a thick layer of the polymer covers the individual fibers in the fabric and prevents strong adhesion of the microorganism to the carrier surface.

The polymerizable vinyl monomer is preferably hydrophobic, rather than hydrophilic, because the carrier used in the present invention must retain a certain degree of hardness (strength) within the liquid culture medium. Exemplary polymerizable vinyl monomers that can be used in the present invention include styrene, vinyl chloride, acrylonitrile, acrylate esters and methacrylate esters such as ethylene glycol methacrylate, tetraethylene glycol dimethacrylate and diethylene glycol dimethacrylate. The vinyl monomer with which the fabric having a network-like structure is impregnated may be polymerized either by catalytic polymerization (thermal method) or by exposure to an ionizing radiation such as of rays. The latter method is preferred to the former method which may cause catalyst contamination or require a prolonged reaction time. If an ionizing radiation is used, the dose rate may be selected from the range of $1 \times 10^4 - 1 \times 10^6$ R/hr to give a total dose of 0.5-1 Mrad. The temperature of irradiation is selected from the range of room temperature ambient to $-100°$ C. More specifically, if the process selected consists of impregnating the fabric having a network-like structure with a polymerizable vinyl monomer, bringing the fabric into contact with a microorganism, and polymerizing said monomer, the fabric is preferably exposed to an ionizing radiation at a low temperature between 0 and $-100°$ C. If a plurality of sheets of the fabric are used, they are preferably subjected to polymerization, with a spacer inserted between each fabric sheet in order to prevent their sticking together.

The process of the present invention for preparing an immobilized microorganism on a carrier made of the fabric shown above having a network-like structure may be carried out by one of the following two techniques. In the first technique, the fabric is impregnated with a polymerizable vinyl monomer, which is then polymerized to form a carrier made of the fabric reinforced with the resulting polymer. This carrier is subsequently brought into contact with a liquid culture medium in which a microorganism is capable of growth, and, thereafter the medium is inoculated with the microorganism. By subsequent culturing, a growing microorganism immobilized on a carrier made of a polymer-reinforced fabric having a network-like structure is obtained. This technique is hereunder sometimes referred to as the two-stage process.

In the two-stage process, a container is first charged with a prepared carrier and liquid culture medium, and then, the medium is inoculated with a given amount of microorganism, and by subsequent culturing under aeration, the microorganism is immobilized onto the carrier. As already mentioned, a plurality of carrier sheets may be used with a spacer inserted between each sheet so as to prevent any cohesion of the sheets. As their respective names suggest, the one-stage process requires only one step for obtaining the desired immobilized microorganism, while the two-stage process requires two steps. However, the yield of the two-stage process can be increased by using a number of immobilizing carriers at a time.

The present invention is described in greater detail by reference to the following examples, to which the scope of the invention is by no means limited.

EXAMPLE 1

Cotton gauze was impregnated with 30% tetraethylene glycol dimethacrylate which was exposed to an ionizing radiation for a dose rate of $1 \times 10^6$ R/hr of $\gamma$-ray at 25° C. for an hour, thereby producing two sheets of carrier ($2 \times 4$ cm) having a network-like structure.

A 200 ml flask was charged with 20 ml of a liquid culture medium containing 1% $KH_2PO_4$, 0.3% $(NH_4)_2SO_4$, 0.3% $NaNO_3$, 0.05% $MgSO_4 \cdot 7H_2O$, 0.5% peptone, 1% cellulose powder and residue water. The previously prepared carrier was added the medium and inoculated with Trichoderma reesei cells, which were subjected to shaking culture at 28° C. On the first day of the cultivation, the cells adhered to the carrier and started to grow. On the 5th and 10th days, cellulase activity (filter paper activity: FPA) in the medium was checked for its ability to decompose cellulose (filter paper). The results were compared with those for the case where no carrier with a network-like structure was used. The data are shown in Table 1.

TABLE 1

| | Cellulase Activity | |
|---|---|---|
| | FPA | |
| Cells | 5 days | 10 days |
| Immobilized growing cells | 1.8 | 2.4 |
| intact cells | 1.2 | 1.8 |

FPA determination consisted of measuring the amount of glucose that formed upon leaving at 50° C. a mixture of a medium (0.5 ml), filter paper (Whatman No. 1, 50 mg) and acetate buffer (1 ml, pH 4.5, 0.1M).

EXAMPLE 2

Cotton gauze was impregnated with 50% diethylene glycol dimethacrylate which was exposed to an ionizing radiation for a dose rate of $1 \times 10^6$ R/hr of $\gamma$-ray at 25° C. for an hour, thereby producing two sheets of carrier ($2 \times 4$ cm) having a network-like structure. A 200-ml flask was charged with 20 ml of a liquid culture medium containing 1.0% $KH_2PO_4$, 0.6% $(NH_4)_2SO_4$, 0.6% $NaNO_3$, 0.1% $CaCl_2$, 0.1% $MgSO_4 \cdot 7H_2O$, 1% maltose and residue water. The previously prepared carrier was added to the medium and inoculated with Rhizopus delemar cells, which were subjected to shaking culture at 26° C. On the second day of the cultivation, the cells immobilized on the carrier surface started to grow rapidly. On the seventh day, the activity of glucoamylase in the culture was determined by measuring the amount of glucose produced in 5 cc of the medium to which 0.5 g of starch is added, after performing enzymatic reaction in the mixture for 1 hr at 30° C. The amount of glucose produced in the intact culture containing no carrier with a network-like structure was also measured. The immobilized growing cells prepared according to the present invention had a higher glucoamylase activity (0.38 g) than the intact cells (0.31 g).

EXAMPLE 3

Cotton gauze was impregnated with 30% of tetraethylene glycol dimethacrylate which was exposed to an ionizing radiation at a dose rate of $1 \times 10^6$ R/hr of electron beams at 25° C. for an hour, thereby producing an immobilizing carrier ($2 \times 4$ cm) having a network-structure, the electron beams being obtained from an electron beam accelerator under the condition of an accelerating voltage of 300 KV and a current of 5mA.

The resulting carrier was inoculated with Trichodenma reesi under the same condition as Example 1 to obtain a Trichodernma reesei immobilized carrier. The cellulose activity of the immobilized carrier is shown in Table 2.

TABLE 2

| Cells | Cellulase Activity FPA | |
|---|---|---|
| | 5 days | 10 days |
| Immobilized growing cells | 1.9 | 2.6 |
| Intact cells | 1.2 | 1.8 |

The FPA determination was in conformity with Example 1.

What is claimed is:

1. A process for preparing a microorganism immobilized on a carrier made of a polymer-coated cotton gauze comprising the following steps:
   (a) impregnating a sheet of cotton gauze having a mesh size of 10-50 with 20-50% weight of ethylene glycol methacrylate;
   (b) irradiating the impregnated gauze with ionizing radiation thereby to polymerize said ethylene glycol methacrylate to obtain a two-dimensional carrier made of a polymer-coated cotton gauze;
   (c) contacting said carrier with a liquid culture medium in which Trichoderma reesei cells can grow;
   (d) inoculating said medium with said cells to culture the cells on said polymer-coated cotton gauze; and
   (e) recovering a polymer-coated cotton gauze comprising the growing cells.

2. The process according to claim 1 wherein the ionizing radiation is selected from the group consisting of gamma rays and X rays, and the radiation is applied at a dosage rate of from $1 \times 10^4$ to $1 \times 10^6$ r/hr to give a total dosage of from 0.5 to 1 Mrad at a temperature ranging from 0 to 100° C.

3. The process according to claim 1 wherein the temperature range is from ambient to 100° C.

* * * * *